United States Patent [19]
Sommermeyer et al.

[11] Patent Number: 6,083,909
[45] Date of Patent: Jul. 4, 2000

[54] HAEMOGLOBIN-HYDROXYETHYL STARCH CONJUGATES AS OXYGEN CARRIERS

[75] Inventors: Klaus Sommermeyer, Rosbach; Wolfram Eichner, Butzbach, both of Germany

[73] Assignee: Fresenius AG, Oberusel, Germany

[21] Appl. No.: 09/214,430

[22] PCT Filed: Jul. 7, 1997

[86] PCT No.: PCT/EP97/03527

§ 371 Date: Jan. 6, 1999

§ 102(e) Date: Jan. 6, 1999

[87] PCT Pub. No.: WO98/01158

PCT Pub. Date: Jan. 15, 1998

[30] Foreign Application Priority Data

Jul. 8, 1996 [DE] Germany .......................... 196 28 705

[51] Int. Cl.⁷ ........................ A61K 38/42; C07K 14/805; C08B 31/18
[52] U.S. Cl. ................................. 514/6; 530/385; 536/105
[58] Field of Search ................................ 514/6; 530/385; 536/105

[56] References Cited

U.S. PATENT DOCUMENTS 4,064,118  12/1977  Wong ....................................... 530/385
5,110,909  5/1992  Dellacherie et al. .................... 530/385

FOREIGN PATENT DOCUMENTS 0 338 916  10/1989  European Pat. Off. .
30 29 307  3/1982  Germany .

*Primary Examiner*—Jeffrey E. Russel
*Attorney, Agent, or Firm*—Nixon & Vanderhye P.C.

[57] ABSTRACT

The present invention relates to new oxygen transfer agents which comprise haemoglobin-hydroxyethylstarch conjugates, and processes for their preparation. The invention furthermore relates to the use of the oxygen transfer agents as a blood substitute, plasma expander, perfusion agent, haemodilution agent and/or cardioplegic solution. The invention relates in particular to oxygen transfer agents which comprise a haemoglobin-hydroxyethylstarch conjugate in which the haemoglobin and the hydroxyethylstarch are linked to one another selectively via amide bonds between free amino groups of the haemoglobin and the reducing end group of the hydroxyethylstarch, which is present in oxidized form.

27 Claims, No Drawings

HAEMOGLOBIN-HYDROXYETHYL STARCH CONJUGATES AS OXYGEN CARRIERS

The present invention relates to new oxygen transfer agents which comprises haemoglobin-hydroxyethylstarch conjugates, and processes for their preparation. The invention furthermore relates to the use of the oxygen transfer agents as a blood substitute, plasma expander, perfusion agent, haemodilution agent and/or cardioplegic solution.

The development of stroma-free haemoglobin solutions, so-called "haemoglobin-based oxygen carriers" (HBOCs), which can be used as a blood substitute has for a long time been an urgent aim of pharmaceutical research and development.

Blood loss, for example as a consequence of an accident or an operation, is in most cases treated with an allogenic blood donation. The associated problems of uncontrolled transfer of pathogenic organisms, in particular of viruses such as HIV or hepatitis pathogens, and the need for blood group typing before the transfusion have been known to the expert for a long time and are described comprehensively in the literature.

An HBOC product which can be used as a standard blood substitute would not only solve these problems, but could furthermore be used as a plasma expander, perfusion agent, haemodilution agent and/or cardioplegic solution.

Although the need for such a product was already recognized early on (cf. Rabiner, J. Exp. Med. 126, (1967) 1127), none of the known HBOC products has so far achieved the status of an approved medicament.

The natural oxygen transfer agent is the blood pigment haemoglobin, a chromoprotein with a molecular weight (MW) of 64 kilodaltons (kDa). The protein comprises two $\alpha$ and $\beta$ peptide chains, each of which has a haem bonded as a prosthetic group. This is a porphyrin ring with a central iron atom. Isolated haemoglobin molecules are very unstable and rapidly dissociate into the more stable $\alpha,\beta$-dimers (MW 32 kDa). The biological half-life of isolated haemoglobin in the blood circulation is about 1 hour, since the dimers are rapidly excreted via the kidneys. The dimers cause nephrotoxic side effects here (cf. Bunn & Jandl, J. Exp. Med. 129, (1967) 925–934).

The HBOC products initially developed also had a nephrotoxic potential, which was attributed to contamination of the products with cell constituents (cf. Relihan, Ann. Surg. 176, (1972) 700).

Furthermore, an isolated haemoglobin composition lacks 2,3-diphosphoglycerate (2,3-DPG), which is the naturally occurring allosteric activator of oxygen bonding. This results in an increased oxygen-bonding affinity of the isolated haemoglobin, and accompanying this a reduced oxygen release capacity of such compositions.

Development work on derivatized haemoglobin molecules was therefore primarily directed at improving the oxygen transfer properties thereof, and by-passing the nephrotoxic symptoms. In this work, haemoglobin was crosslinked intramolecularly, linked intermolecularly to form polymeric HBOC forms and/or coupled to polymers to provide conjugated HBOC forms. In this work, mixed forms of intra- and intermolecularly crosslinked haemoglobin derivatives have also been prepared and investigated for the planned use.

Crosslinking of haemoglobin by means of bi- or polyfunctional crosslinking agents can take place selectively or non-selectively. In one form of selective crosslinking, two protein chains of the haemoglobin are bonded intramolecularly with one another, as a result of which the natural tetrameric form of the isolated haemoglobin molecule is stabilized. By choosing a suitable crosslinking agent, the oxygen affinity of the haemoglobin can bond oxygen reversibly under physiological conditions. Examples of such crosslinking agents are pyridoxal phosphate and diaspirin, and derivatives thereof. Processes for crosslinking haemoglobin are described, for example, in Benesch (Meth. Enzymol., vol. 231 (1994), 267–274), Keipert et al. (Transfusion, vol. 29 (1989), 767–773), Synder et al. (Proc. Natl. Acad. Sci. USA, 84, (1987), 7280–7284) and in Rogers et al. (Biochim. et Biophys. Acta, 1248 (1995), 135–142).

In a non-selective crosslinking, intermolecularly crosslinked, polymeric HBOC products are formed. Appropriate crosslinking agents and processes for their use are described, for example, in DE-26 07 706, EP-0 646 130 and Hai et al. (Art. Cells, Blood Subs. and Immob. Biotech, 22(3) (1994), 923–931). An overview of various haemoglobin derivatives and the problems associated with clinical use is given in the publications by Gould et al., Transfus. Sci. 16, (1995) 5–17, and Chang et al., Biomat. Art. Cells & Immob. Biotech., 20, (1992) 159–179.

Known haemoglobin conjugates are described comprehensively in Xue and Wong (Meth. in Enzymol., 231 (1994), p. 308–322) and, for example, in DE 26 16 086 or DE 26 46 854. The latter discloses processes by means of which haemoglobin is bonded to hydroxyethylstarch, by first reacting hydroxyethylstarch with sodium periodate. Dialdehydes are formed in this reaction, and the haemoglobin is bonded to these. In contrast, DE 26 16 086 describes the coupling of haemoglobin to hydroxethylstarch by a process in which a crosslinking agent (e.g. cyanogen bromide) is first bonded to the hydroxyethylstarch, and haemoglobin is then bonded to the intermediate product.

The oxygen-bonding affinity of the haemoglobin derivative also depends on the ligand of the haem group during the crosslinking and/or polymerization, as well as on the choice of suitable crosslinking and/or polymerization agents. Oxyhaemoglobin oxidizes rapidly to met-haemoglobin (Fe-III), which has to high an oxygen-bonding affinity to be suitable as an oxygen transfer agent. The processes mentioned for the preparation of HBOC derivatives have therefore also been carried out with partly or completely deoxygenated haemoglobin (cf. Benesch, R. E. loc. cit.).

However, the processes to date for the preparation of crosslinked and/or conjugated HBOC products have not rendered possible selective bonding of haemoglobin to the particular polymer. In all processes, a mixture of copolymers, the constituents of which had different biological activities, was formed. It has so far been possible for the reaction product or the composition of the mixture to the characterized only roughly. Both the higher molecular weight products (MW>500 kDa) and residual tetrameric forms caused toxic side effects. The removal of the particular low and/or high molecular weight portions from the HBOC products, for example by additional filtration steps, causes considerable losses in yield, as a result of which the profitability of the preparation process is impaired considerably.

The HBOC products tested to date additionally had vascular side effects which, according to the latest clinical studies, are to attributed to low molecular weight, i.e. substantially tetrameric, HBOC forms (cf. Gould et al., loc. cit., and Alayash & Cashon, Molecular Medicine Today, 1, (1995) 122–127). These low molecular weight HBOC forms are capable of passing from the blood circulation into the endothelial cell layers of the blood vessels. The high bonding affinity of haemoglobin for nitric oxide (NO, also known as endothelial derived relaxing factor, EDRF) causes the amount of NO freely available in this tissue to be reduced drastically after administration of HBOC derivatives. As a consequence of the local reduction in the NO concentration, a systemic vasoconstriction develops, leading to hypertension.

Jia et al. (Nature, 380, (1996) 221–226) even attribute a central role in regulation of the NO circulation to haemoglobin. According to them, haemoglobin is oxygenated and S-nitrosylated cooperatively in the lung. During arteriovenous transfer, the NO group is transferred to other proteins, which as a result acquire an NO-like vasodilating activity. However, as a rule crosslinked HBOC products no longer have cooperative properties.

Another toxic activity of the HBOC products tested to date was described, inter alia, by Alayash and Cahsom (cf. Molec. Med. Today, (1995) loc. cit.). According to them, haemoglobin molecules outside the erythrocytes participate in redox reactions, in the course of which highly reactive species of haemoglobin and oxygen are formed, these being held responsible, inter alia, for lipid peroxidation.

To suppress the toxic side effects of the HBOC products tested to date, forms of administration in which haemoglobin is packed in liposomes were developed, synthetic erythrocyte-like transfer organelles for haemoglobin resulting (cf. Rudolph et al., Crit. Care Med. 22, (1994) 142–150). However, the introduction of high amounts of phospholipids into the blood circulation is associated with a further risks for patients.

Summarizing, it can be said that the HBOC products tested to date have not obtained approval as medicaments, since their clinical use as oxygen transfer agents has so far been prevented by an inadequate tolerability.

The object of the present invention was therefore to provide an oxygen transfer agent which can be used clinically as a blood substitute. Another object of this invention is to provide a suitable preparation process for the oxygen transfer agent according to the invention.

This object is achieved by an oxygen transfer agent which comprises a haemoglobin-hydroxyethylstarch conjugate in which haemoglobin and the hydroxyethylstarch are linked to one another selectively via amide bonds between free amino groups of the haemoglobin and the reducing end group of the hydroxyethylstarch, which is present in oxidized form.

It has been found, surprisingly, that haemoglobin-hydroxyethylstarch conjugates according to the invention are outstandingly suitable as oxygen transfer agents, since they are tolerated particularly well. The agent has an oxygen-bonding affinity which allows reversible bonding of oxygen under physiological conditions ($P_{50}$ of 20 to 80 mm Hg, preferably 20 to 50 mm Hg; the determination of $P_{50}$ being carried out at maximum enrichment with pure oxygen—at least 150 mm Hg). The haemoglobin-hydroxyethylstarch conjugate is too large to penetrate into the endothelial cell layers of the blood vessels, and therefore causes no hypertensive side effects. The oxygen transfer agent comprises neither antigenic nor pyrogenic constituents, and also causes no nephrotoxic side effects.

According to the invention, it has been found, surprisingly, that the advantageous rheological properties which have made hydroxyethylstarch a preferred agent for haemodilution and for volume substitution (cf. Weidler et al., Arzneim.-Forschung/Drug Res., 41, (1991) 494–498) are retained in the conjugate. The good tolerability of the oxygen transfer agent is therefore also based on a surprising combination of the advantageous oxygen transfer properties of haemoglobin and the haemodilution properties of hydroxyethylstarch.

The oxygen transfer agent has along vascular persistence, and the surface of the haemoglobin molecule is shielded by substituents. Surprisingly, it has been found that in the haemoglobin-hydroxyethylstarch conjugate according to the invention, the haemoglobin is prevented by this shielding effect from participating in toxic redox reactions.

Another advantage of the oxygen transfer agent according to the invention is that hydroxyethylstarch and haemoglobin as a conjugate can be administered in high concentrations simultaneously, without the colloidal osmotic pressure being increased as a result.

The oxygen transfer agent comprises the haemoglobin-hydroxyethylstarch conjugate in a concentration of between 2 and 40 g/dl, preferably in a concentration of between 5 and 20 g/dl, and particularly preferably in a concentration of 8 to 20 g/dl. The oxygen transfer agent can furthermore comprise known physiologically tolerated carriers, diluents or excipients.

In the context of the present invention, preferably stroma-free, purified and pasteurized haemoglobin, which can be obtained by processes described comprehensively in the prior art, is used for the preparation of the haemoglobin-hydroxyethylstarch conjugate. The haemoglobin can be crosslinked and/or polymerized. The haemoglobin can be of human, animal, vegetable or recombinant origin. In the context of the present invention, it has been found, surprisingly, that the shielding effects of the hydroxyethylstarch prevent the immunological complications which would be expected if animal haemoglobin is used. A preferred embodiment of the invention therefore relates to an oxygen transfer agent which comprises a haemoglobin-hydroxyethylstarch conjugate in which the haemoglobin is of animal origin. The haemoglobin can be, for example, of bovine, porcine or equine origin. According to a particularly preferred embodiment of the invention, bovine haemoglobin, which has the preferred oxygen-bonding affinity in isolated form even without crosslinking, is used for the preparation of the haemoglobin-hydroxyethylstarch conjugate.

If human haemoglobin is used, this should be stabilized in the tetrameric form by means of crosslinking, human haemoglobin is rendered capable simultaneously of reversible oxygen bonding under physiological conditions. A large number of processes for crosslinking or polymerization are known to the expert. According to the invention, any desired process can be used, as long as the haemoglobin is stabilized and obtains the desired oxygen affinity ($P_{50}$ of 20 to 80 mm Hg, preferably $P_{50}$ of 20 to 50 mm Hg) as a result. Preferred crosslinking processes include intramolecular crosslinking with bis-pyridoxal tetraphosphate (cf. Keipert et al., Transfusion, vol. 29 (1989), 767–773) or diaspirin (cf. Snyder et al., Proc. Natl. Acad. Sci. USA, 84 (1987), 7280–7284) or crosslinking and polymerization with oxidized raffinose (cf. EP-0 646 130).

According to a particularly preferred embodiment of the invention, before the coupling to the hydroxyethylstarch the haemoglobin is present in deoxygenated or partly deoxygenated form. In the case of partly deoxygenated forms, compositions which comprise deoxy-haemoglobin to the extent of 20 to 80% and haemoglobin in other derivative states to the extent of 80 to 20% are preferred, compositions of 50 to 80% deoxy-haemoglobin and 50 to 20% haemoglobin in other derivative states being particularly preferred. Other derivative states of haemoglobin here are, in particular, CO—, oxy- and/or methaemoglobin derivatives.

To prepare the conjugate, preferably hydroxyethylstarch which has an average molecular weight of 1 to 40 kDa is used, hydroxyethylstarch having an average molecular weight of 2 to 20 kDa being preferred, and hydroxyethylstarch having an average molecular weight of 5 to 20 kDa being particularly preferred. Preferred hydroxyethylstarch is furthermore characterized by a molar degree of substitution of 0.1 to 0.8 and a ratio of $C_2:C_6$ substitution in the range from 2 to 20.

Hydroxyethylstarch which is preferred according to the invention can be obtained from a commercially obtainable (Sigma) hydroxyethylstarch of comparatively higher molecular weight by acid hydrolysis, for example with HCl. The hydroxyethylstarch is then subjected to a precipiation reaction, in which, for example, acetone can be used.

The molecular weight of the haemoglobin-hydroxyethylstarch conjugate according to the invention depends on the molecular weight or molecular weight distribution of the haemoglobin employed, the molecular weight distribution of the hydroxyethylstarch employed and the choice of reaction conditions. According to the invention, haemoglobin-hydroxyethylstarch conjugates with a molecular weight of between 100 and 700 kDa are preferred, a molecular weight of between 200 and 300 kDa being particularly preferred.

In the context of the present invention, it has been found that the known stabilizing effect of saccharides on haemoglobin (cf. Rudolph, Cryobiology, 25, (1988) 1–8) also arises from the hydroxyethylstarch of the conjugate if short-chain hydroxyethylstarch is used. Oxygen transfer agents according to the invention therefore have an improved storage stability at 4° C. and at room temperature, compared wit non-modified HBOC products. The oxygen transfer agent therefore itself has surprisingly become a carrier of the advantageous stabilizing properties of saccharides.

The present invention also relates to the processes for the preparation of the oxygen transfer agents which comprise a haemoglobin-hydroxyethylstarch conjugate. These processes allow for the first time selective bonding of haemoglobin to hydroxyethylstarch, as a result of which an oxygen transfer agent is formed. The conjugate is prepared in a multi-stage process, in which the reducing end groups of hydroxyethylstarch are first oxidized and haemoglobin is then coupled to the oxidized end groups of the hydroxyethylstarch via free amino groups by means of amide bonds.

The starting material used for the process is preferably hydroxyethylstarch having an average molecular weight of 1 to 40 kDa, hydroxyethylstarch having an average molecular weight of 2 to 20 kDa being preferred, and hydroxyethylstarch having an average molecular weight of 5 to 20 kDa being particularly preferred, Preferred hydroxyethylstarch is furthermore characterized by a molar degree of substitution of 0.1 to 0.8 and a ratio of $C_2:C_6$ substitution in the range from 2 to 20.

In the context of the invention, stroma-free, purified, pasteurized, crosslinked and/or polymerized haemoglobin is preferably used for the preparation of the oxygen transfer agent. The haemoglobin here can be of human, animal, vegetable or recombinant origin. In the context of the present invention, bovine haemoglobin is preferred, since in the isolated form it has an oxygen-bonding affinity which allows reversible oxygen bonding under physiological conditions.

According to a preferred process of the invention, the reducing end groups of the hydroxyethylstarch are oxidized by first mixing the hydroxyethylstarch with an iodine-containing solution and then adding potassium hydroxide solution.

According to another preferred process of the invention, the haemoglobin is bonded to the oxidized end groups of hydroxyethylstarch in a second step. The reaction can be carried out, for example, by mixing the individual components at 40° C. A nucleophilic substitution reaction takes place here between a free amino group of the haemoglobin and the lactone of the hydroxyethylstarch, to form an amide bond by which the haemoglobin is bonded to the oxidized reducing end group of the hydroxyethylstarch.

According go the invention, it has accordingly been found, surprisingly, that, by the process of Hashimoto et al. (Kunstoffe Kautschuk, Fasern, 9, (1992) 1271–1279) for the preparation of block copolymers from polysaccharides and polyamides, purified haemoglobin, which can be crosslinked intra- and/or intermolecularly, can be bonded on to oxidized hydroxyethylstarch such that a particularly tolerated oxygen transfer agent is formed. Using the doctrine according to the invention, for the first time the synthesis of a haemoglobin conjugate can be controlled to the extent that tetrameric haemoglobin forms are bonded to hydroxyethylstarch without a noticeable content of undesirable high molecular weight haemoglobin forms resulting.

According to a preferred embodiment of the invention, the reactions conditions are chosen such that a haemoglobin-hydroxyethylstarch conjugate which has a molecular weight of between 80 and 800 kDa is formed, a molecular weight of between 100 and 500 kDa, and in particular between 150 and 400 kDa, being preferred.

An approximately quantitative reaction of the haemoglobin with the hydroxyethylstarch takes place by the preparation process according to the invention. Scarcely any low molecular weight haemoglobin forms therefore also remains in the reaction batch, a content of less than 5% non-conjugated haemoglobin forms being preferred. Accordingly, in another preferred embodiment of the invention, no expensive purification process to isolate the desired reaction product is necessary after the coupling of haemoglobin and hdroxyethyl-starch.

According to another preferred embodiment of the invention, before the coupling to the hydroxyethylstarch the haemoglobin is present in either completely deoxygenated or partly deoxygenated form. In the case of a partly deoxygenated form, compositions which comprise deoxy-haemoglobin to the extent of 20 to 80% and haemoglobin in other derivative states to the extent of 80 to 20% are preferred, compositions of 20 to 80% deoxy-haemoglobin and 80 to 20% haemoglobin in other derivative states being particularly preferred.

The deoxygenation of the haemoglobin can be carried out by means of any desired chemical or physical processes. In these, haemoglobin is either treated with chemical reducing agents, such as Na ascorbate, glutathione, N-acetyl-cysteine or N-acetyl-methionine, or circulated against an inert gas, such as $N_2$, He or Ar, by means of a membrane which is permeable to gas.

In a particularly preferred process, cysteine or acetyl-cysteine is used as the reducing agent. The reduction is carried out until the oxy-haemoglobin content is less than 5%, a content of less than 1% being preferred. The content of met-haemoglobin should be less than 5%, a content of less than 3 or 1%, and in particular a content of less than 0.5%, being preferred.

According to another particularly preferred embodiment of the invention, a haemoglobin solution in which the haemoglobin comprises deoxy-haemoglobin to the extent of 20 to 80% and haemoglobin in other derivative states to the extent of 80 to 20% is used for the preparation of the haemoglobin-hydroxyethylstarch conjugate. To prepare such a haemoglobin solution, oxy-haemoglobin can be partly deoxygenated, or deoxy-haemoglobin can be partly oxygenated. According to the derivative form of the starting haemoglobin solution and the desired haemoglobin derivative composition preferred according to the invention, a haemoglobin solution furthermore can either be converted into the stable CO form with carbon monoxide gas, and/or oxygenated with oxygen or $O_2$-containing gases, and/or be deoxygenated with nitrogen or other inert gases. The gas exchange here can be carried out by any desired processes described in the prior art. Preferred processes include gassing of a deoxy-haemoglobin solution with oxygen or with a gas containing oxygen, or chemical partial reduction of the oxy-haemoglobin with a reducing agent, such as, for example, Na dithionate, Na ascorbate or Na bisulphite.

When the reaction has ended, the reducing agent can be separated off, for example by ultrafiltration. In a preferred embodiment of the invention, the ultrafiltration is carried out by means of a membrane which keeps back the desired product in the retained material.

According to a particularly preferred process of the invention, the haemoglobin is then lyophilized with gassing with $N_2$.

In another particularly preferred embodiment of the invention, hydroxyethylstarch is oxidized selectively on the reducing end groups by first adding a 0.1 N iodine solution to an aqueous solution of fractionated hydroxyethylstarch (MW$\leq$10 kDa). 0.1 N KOH solution is then added at room temperature (RT), until the colour originating from the iodine disappears. This step is repeated once or several times, and the mixture is then stirred for a further 30 minutes. Thereafter, the solution is subjected to dialysis, the dialysis membrane having an exclusion volume which keeps back the desired product (in this case oxidized hydroxyethylstarch) in the retained material. After purification by chromatography through a cation exchanger column, the solution is lyophilized, it also being possible to carry out the cation exchange chromatography before the dialysis.

According to another particularly preferred embodiment of the invention, the bonding of the haemoglobin to the selectively oxidized hydroxyethylstarch is carried out by first taking up the haemoglobin in DMSO or other suitable non-aqueous solvents and transferring the mixture to a three-necked round-bottomed flask. For this, a solution taken up in DMSO is added slowly at 40° C. to a hydroxyethylstarch oxidized by the above processes. However, these steps can be carried out in any desired sequence, that is to say haemoglobin can also be added to a hydroxyethylstarch solution.

After stirring at 40° C. for 25 hours, the residue is purified by gel permeation chromatography (GPC) or dialysis and/or ultrafiltration and freed from the solvent in this way. The increase in the molecular weight of the haemoglobin preparations can be determined directly by means of SDS-PAGE and non-denaturing gel electrophoresis or ultracentrifugation (density gradient or sedimentation equilibrium centrifugation). The usual chromatographic methods, such as SEC (size exclusion chromatography) or thin layer chromatography (TLC) are furthermore suitable for determining the molecular size. It is possible to use affinity chromatography methods (HIC, RPC) and IEC (ion exchange chromatography), as well as IEF (isoelectronic focusing) for determining modification-related changes in the physico-chemical properties of the molecules. The degree of substitution can be quantified by $^1$H-NMR, $^{13}$C-NMR, mass spectrometry or capillary electrophoresis (CE). The colorimetric method for determination of free amino groups in proteins by means of TNBS (Habeeb et al., Anal. Biochem., 14, 328 [1966]) in combination with a protein test (Bradford, Lowry, Biuret) or Kjeldahl nitrogen determination is furthermore suitable for this purpose.

The invention also relates to oxygen transfer agents which comprise haemoglobin-hydroxyethylstarch conjugate and albumin. The albumin here can be of human, animal or recombinant origin and is preferably employed as an aqueous solution. The oxygen transfer agent preferably comprises albumin in a concentration of between 2 and 20 g/dl, concentrations of between 5 and 15 g/dl being preferred.

The weight ratio of haemoglobin-hydroxyethylstarch conjugate to albumin in oxygen transfer agents which are preferred according to the invention can be 1:10 to 4:1. Since the albumin is considerably less expensive than the conjugate and can be used to achieve the desired osmotic pressure in the oxygen transfer agent, oxygen transfer agents with a comparatively high content of albumin and a low content of haemoglobin-hydroxyethylstarch conjugates are particularly preferred.

The invention furthermore relates to oxygen transfer agents which comprise haemoglobin-hydroxyethylstarch conjugates and albumin and have a particular good vascular tolerability. According to a particularly preferred embodiment of the invention, for this the conjugates described are mixed with albumin, preferably with human serum albumin, which has been saturated with nitrogen monoxide beforehand. Haemoglobin and albumin have the property of complexing NO in the N-nitroso form (cf. Keaney et al., J. Clin. Invest., 91., (1993) 1582–1589). As a rule crosslinked HBOC products no longer have cooperative properties. They therefore lack the capacity for cooperative NO bonding. In the context of the present invention, it has been found, surprisingly, that this deficiency of haemoglobin-hydroxyethylstarch conjugates can be compensated by using an oxygen transfer agent which, in addition to the conjugate, comprises an albumin solution which has complexed NO. The saturation of albumin with NO here is carried out by gassing an albumin solution with NO with exclusion of oxygen. The vascular tolerability of the product is further improved as a result.

The present invention particularly relates to the use of the oxygen transfer molecules according to the invention and of the compositions of the haemoglobin-hydroxyethylstarch conjugates and albumin as a blood substitute, plasma expander, perfusion agent, haemodilution agent and/or as a cardioplegic solution.

EXAMPLE

Preparation of a haemoglobin-hydroxyethylstarch conjugate

A.1 Oxidation of the reducing and groups of hydroxyethylstarch:

In a preferred process of the invention, the reducing end groups of the hydroxyethylstarch are oxidized selectively. 2 ml of a 0.1 N iodine solution were first added dropwise to a solution, taken up in less than 3 ml deionized water, of fractionated hydroxyethylstarch (MW$\leq$4 kDa; weighed amount approx. 0.56 mmol). Approx. 3.3 ml of a 0.1 N KOH solution were then added at room temperature, until the colour originating from the iodine disappeared. By repeating the above step, 14 ml iodine solution and 23 ml KOH solution were added to the reaction batch, and the mixture was then stirred for a further 30 min.

The solution was then purified by chromatography on a cation exchanger column (Amberlite IR 120, $H^+$ form).

After diafiltration over a regenerated cellulose membrane (Millipore PLAC 076 10) with an exclusion limit of 1,000 Da, the partly concentrated solution was lyophilized. However, the cation exchange chromatography can also be carried out after the diafiltration. The yield was of the order of 80–90%.

A.2 Alternative process for the oxidation of the reducing end groups of hydroxyethylstarch:

2 ml of a 0.1 N iodine solution were first added dropwise to a solution, taken up in less than 3 ml deionized water, of fractionated hydroxyethylstarch (MW≦10 kDa; approx. 5 g). 0.1 N KOH solution was then added at room temperature (RT), until the colour originating from the iodine disappeared. By repeating the above step, 14 ml iodine solution and 23 ml KOH solution were added to the reaction batch, and the mixture was then stirred for a further 30 min. Thereafter, the solution was subjected to dialysis with an exclusion volume of the dialysis membrane of about 9 kDa. After purification by chromatography on a cation exchanger column (Amberlite IR-120), the solution was lyophilized. The yield was of the order of 85%.

B.1 Deoxygenation of haemoglobin by gassing:

Bovine haemoglobin in a concentration of 6 g/dl in 0.5 M NaCl, 0.1 M $Na_2HPO_4$ and 0.05 M $NaHCO_3$ was deoxygenated by gassing. The haemoglobin was initially present in the CO form to the extent of 94 to 96%. The deoxygenation was carried out in a closed container, in which the haemoglobin solution was circulated over a gas exchanger, while the membrane was gassed continuously first with $O_2$ for partial oxygenation and then with $N_2$ under a pressure of 10 psi. The deoxygenation was ended at a content of 70% deoxy-haemoglobin. The haemoglobin was then lyophilized with gassing with $N_2$.

B.2 Deoxygenation of haemoglobin by means of chemical reducing agents:

Bovine haemoglobin in a concentration of 6 g/dl in 0.5 M NaCl, 0.1 M $Na_2HPO_4$ and 0.05 M $NaHCO_3$ was reduced chemically. For this, 100 mM Na disulphite were added to the haemoglobin solution. After one hour, the resulting solution comprised deoxy-haemoglobin to the extent of 75%. The Na disulphite was separated off by means of ultrafiltration at a membrane exclusion limit of 50 kDa. The haemoglobin was then lyophilized with gassing with $N_2$.

C. Coupling of haemoglobin to the oxidized end groups of hydroxyethylstarch:

In each case about 1 to 1.5 g of the haemoglobin prepared in steps B.1 and B.2 were taken up in 15 ml DMSO and the mixture transferred to a 100 ml three-necked round-bottomed flask. A solution, taken up in 0.5 ml DMSO, of hydroxyethylstarch oxidized according to A. was added slowly at 40° C. After stirring at 40° C. for one to two days, the residue was free from the solvent by dialysis and partly concentrated with the aid of diafiltration. The purity of the product, in particular the removal of starting substances, can be further improved by incorporating standard chromatography methods and ultrafiltration.

The success of the coupling reaction was detected with the aid of gel permeation chromatography.

We claim:

1. Oxygen transfer agent comprising a haemoglobin-hydroxyethylstarch conjugate, characterized in that the haemoglobin and the hydroxyethylstarch in the conjugate are linked to one another selectively via amide bonds between free amino groups of the haemoglobin and the reducing end group of the hydroxyethylstarch, which is present in oxidized form.

2. Oxygen transfer agent according to claim 1, characterized in that the haemoglobin-hydroxyethylstarch conjugate is present in the oxygen transfer agent in a concentration of between 2 and 20 g/dl.

3. Oxygen transfer agent according to claim 2, characterized in that the haemoglobin-hydroxyethylstarch conjugate is present in the oxygen transfer agent in a concentration of between 5 and 20 g/dl.

4. Oxygen transfer agent according to claim 1, characterized in that the haemoglobin is of human, animal, vegetable or recombinant origin.

5. Oxygen transfer agent according to claim 1, characterized in that the haemoglobin is of bovine origin.

6. Oxygen transfer agent according to claim 1, characterized in that before linking the hydroxyethylstarch, the haemoglobin is present as deoxy-haemoglobin or as a mixture of deoxy-haemoglobin and haemoglobin in a CO—, $O_2$— or met-haemoglobin derivative state.

7. Oxygen transfer agent according to claim 1, characterized in that before linking the hydroxyethylstarch, the haemoglobin is present as a mixture of deoxy-haemoglobin and oxy-haemoglobin, the content of deoxy-haemoglobin being 20 to 80% and the content of haemoglobin in a CO—, $O_2$— or met-haemoglobin derivative state being 80 to 20%.

8. Oxygen transfer agent according to claim 1, characterized in that the haemoglobin is crosslinked and/or polymerized haemoglobin.

9. Oxygen transfer agent according to claim 1, characterized in that the hydroxyethylstarch has an average molecular weight of 1 to 40 kDa.

10. Oxygen transfer agent according to claim 1, characterized in that the hydroxyethylstarch has an average molecular weight of 2 to 20 kDa.

11. Oxygen transfer agent according to claim 1, characterized in that the hydroxyethylstarch has a molar degree of substitution of 0.1 to 0.8 and a ratio of $C_2:C_6$ substitution in the range from 2 to 20, based on the hydroxyethyl groups.

12. Oxygen transfer agent according to claim 1, characterized in that the agent furthermore comprises albumin.

13. Oxygen transfer agent according to claim 12, characterized in that the albumin is serum albumin of human, animal, vegetable or recombinant origin.

14. Oxygen transfer agent according to claim 12, characterized in that the albumin is present in a concentration of between 2 and 20 g/dl.

15. Oxygen transfer agent according to claim 12, characterized in that the weight ratio of the haemoglobin-hydroxyethylstarch conjugate to albumin is in the range from 1:10 to 4:1.

16. Oxygen transfer agent according to claim 12, characterized in that before addition to the conjugate, the albumin is present in an aqueous solution saturated with nitrogen monoxide (NO).

17. Oxygen transfer agent according to claim 1, characterized in that the agent is present as an aqueous solution or as a lyophilisate.

18. Process for the preparation of an oxygen transfer agent comprising a haemoglobin-hydroxyethylstarch conjugate, characterized in that the reducing end groups of hydroxyethylstarch are first oxidized and haemoglobin is then coupled to the oxidized end groups of the hydroxyethylstarch via free amino groups by means of amide bonds.

19. Process according to claim 18, characterized in that the oxidation of the reducing end groups of the hydroxyethylstarch is carried out by first mixing the hydroxyethylstarch with an iodine-containing solution and then adding potassium hydroxide solution.

20. Process according to claim 18, characterized in that the coupling of the free amino groups of the haemoglobin with the reducing end groups of the hydroxethylstarch which are present in oxidized form is carried out by mixing the individual components at 40° C.

21. Process according to claim 18, characterized in that the haemoglobin is of human, animal, vegetable or recombinant origin.

22. Process according to claim 18, characterized in that the haemoglobin is of bovine origin.

23. Process according to claim 18, characterized in that before the coupling to the hydroxyethylstarch, the haemoglobin is present as deoxy-haemoglobin or as a mixture of deoxy-haemoglobin and haemoglobin in a CO—, $O_2$— or met-haemoglobin derivative state.

24. Process according to claim 18, characterized in that before the coupling to the hydroxyethylstarch, the haemoglobin is present as a mixture of deoxy-haemoglobin and haemoglobin in a CO—, $O_2$— or met-haemoglobin derivative state, the content of deoxy-haemoglobin being 20 to 80% and the content of haemoglobin in said derivative state being 80 to 20%.

25. Process according to claim 18, characterized in that the haemoglobin is crosslinked and/or polymerized haemoglobin.

26. Process according to claim 18, characterized in that the hydroxyethylstarch has an average molecular weight of 5 to 40 kDa, a molar degree of substitution of 0.1 to 0.8 and a ratio of $C_2$:$C_6$ substitution in the range from 2 to 20, based on the hydroxyethyl groups.

27. A method of treating a mammal in need of an oxygen transfer comprising administering an oxygen transfer agent according to claim 1 or an oxygen transfer agent prepared according to claim 18 with a blood substitute, plasma expander, perfusion agent, haemodilution agent and/or cardioplegic solution to said mammal.

* * * * *